(12) United States Patent
Utterberg et al.

(10) Patent No.: US 8,450,553 B2
(45) Date of Patent: May 28, 2013

(54) INJECTION AND HEMOSTASIS SITE

(75) Inventors: David S. Utterberg, Seattle, WA (US); William J. Schnell, Libertyville, IL (US); David Bell, Grayslake, IL (US)

(73) Assignee: DSU Medical Corporation, Seattle, WA (US)

( * ) Notice: Subject to any disclaimer, the term of this patent is extended or adjusted under 35 U.S.C. 154(b) by 2024 days.

(21) Appl. No.: 11/218,220

(22) Filed: Sep. 1, 2005

(65) Prior Publication Data

US 2006/0079823 A1   Apr. 13, 2006

Related U.S. Application Data

(63) Continuation-in-part of application No. 10/943,106, filed on Sep. 16, 2004, now Pat. No. 8,017,826.

(51) Int. Cl.
*A61F 13/00* (2006.01)
*A61M 5/32* (2006.01)

(52) U.S. Cl.
USPC ............... 602/53; 602/42; 602/43; 604/174; 604/180

(58) Field of Classification Search
USPC ............... 604/304, 180, 174; 602/53, 41–43, 602/58; 433/2, 8, 22; 606/201–204, 213
See application file for complete search history.

(56) References Cited

U.S. PATENT DOCUMENTS

| | | | |
|---|---|---|---|
| 3,367,332 A | 2/1968 | Groves | |
| 3,490,448 A * | 1/1970 | Grubb | 602/53 |
| 3,952,735 A | 4/1976 | Wirtschafter et al. | |
| 3,954,109 A | 5/1976 | Patel | |
| 4,053,053 A | 10/1977 | Tumangday | |
| 4,123,409 A | 10/1978 | Kaelble | |
| 4,182,338 A | 1/1980 | Stanulis | |
| 4,224,945 A | 9/1980 | Cohen | |
| 4,233,980 A | 11/1980 | McRae et al. | |
| 4,336,806 A | 6/1982 | Eldridge | |
| 4,377,159 A * | 3/1983 | Hansen | 602/53 |
| 4,675,006 A | 6/1987 | Hrushesky | |
| 4,915,694 A | 4/1990 | Yamamoto et al. | |
| 4,978,342 A | 12/1990 | Heimreid | |
| 4,988,341 A | 1/1991 | Columbus et al. | |
| 5,015,228 A | 5/1991 | Columbus et al. | |
| 5,236,421 A | 8/1993 | Becher | |

(Continued)

OTHER PUBLICATIONS

Shore data comparison chart (Internet, Apr. 29, 2009, 2 pages).

(Continued)

*Primary Examiner* — Kim M Lewis
(74) *Attorney, Agent, or Firm* — Seyfarth Shaw LLP

(57) ABSTRACT

A pad of elastomeric material having a softness of no more than about durometer 50 Shore 00. The pad may carry adhesive and/or a housing for adhering the pad to a surface, either directly or indirectly through an envelope which surrounds the pad and carries the adhesive. Such a pad exhibits hemostatic and leak prevention properties against needle puncture holes in the skin or the wall of a hollow medical device. Particularly, hemostasis may be prevented with low pressure application of the pad to the skin. The pad may be previously applied to the skin of the patient or a wall of a medical device such as tubing or a solution bag, and the needle may then penetrate both the pad and the skin or medical device wall, to make a resealable puncture with leakage reduction and hemostasis when the needle is withdrawn.

27 Claims, 3 Drawing Sheets

U.S. PATENT DOCUMENTS

| | | | |
|---|---|---|---|
| 5,259,835 A | 11/1993 | Clark et al. | |
| 5,263,965 A | 11/1993 | Roth | |
| 5,496,264 A | 3/1996 | Watson et al. | |
| 5,508,334 A * | 4/1996 | Chen | 524/474 |
| 5,569,207 A | 10/1996 | Gisselberg et al. | |
| 5,639,810 A | 6/1997 | Smith | |
| 5,647,357 A | 7/1997 | Barnett | |
| 5,690,610 A | 11/1997 | Ito et al. | |
| 5,728,071 A * | 3/1998 | Watson et al. | 604/180 |
| 5,738,641 A | 4/1998 | Watson et al. | |
| 5,810,756 A | 9/1998 | Montecalvo et al. | |
| 5,840,052 A | 11/1998 | Johns | |
| 5,891,074 A | 4/1999 | Cesarczyk | |
| 5,994,450 A * | 11/1999 | Pearce | 524/505 |
| 6,005,159 A | 12/1999 | Spier | |
| 6,007,562 A | 12/1999 | Harren et al. | |
| 6,036,721 A | 3/2000 | Harren et al. | |
| 6,051,747 A * | 4/2000 | Lindqvist et al. | 602/46 |
| 6,093,468 A | 7/2000 | Toms et al. | |
| 6,117,176 A | 9/2000 | Chen | |
| 6,441,265 B1 * | 8/2002 | Chan | 602/53 |
| 6,524,284 B1 | 2/2003 | Marshall | |
| 6,932,963 B2 * | 8/2005 | Perricone | 424/59 |
| 7,093,599 B2 | 8/2006 | Chen | |
| 2003/0175323 A1 | 9/2003 | Utterberg et al. | |
| 2007/0225652 A1 | 9/2007 | Scherr | |

OTHER PUBLICATIONS

US 5,051,228, Columbus et al. (withdrawn).
Vita Clip Brochure (6 pages).
Website print-out of www.datascope.com; 2 pgs, Dec. 8, 2005.

* cited by examiner

INJECTION AND HEMOSTASIS SITE

This is a continuation-in-part of U.S. patent application Ser. No. 10/943,106, filed Sep. 16, 2004 now U.S. Pat. No. 8,017,826.

BACKGROUND OF THE INVENTION

Generally, when the needle or catheter penetrates the skin for access to an artery, a vein, or a fistula as in hemodialysis, there is a certain amount of bleeding that takes place when it is removed. In blood donation, for example, when the donor needle is removed, the donor is asked to elevate his or her arm and to press cotton gauze against the needle penetration site for some minutes, until the wound has completely clotted.

In the field of extracorporal blood processing such as hemodialysis, larger diameter needles, such as 15 gauge needles, are used rather than the smaller needles used for blood collection and blood sampling. The blood pressure is higher due to the fistula's arterialized vein structure, and the patient is anticoagulated for the extracorporeal procedure. Thus, when the needle is withdrawn, bleeding is more pronounced, and must be dealt with more rigorously, to avoid the loss of a significant amount of blood through bleeding. Since hemodialysis in particular is performed frequently on chronic patients, even small blood losses can add up, so that it would be desirable to minimize the bleeding to avoid the relatively small amount of blood that is conventionally lost when dialysis needles are withdrawn.

Generally, compression is used for a period of time after withdrawal of any hollow bore needle, to achieve hemostasis. Typically, this is done with absorbent gauze manually pressed over the cannulation site as soon as the needle is removed. As the gauze is absorbent, this method does not staunch bleeding, but merely creates a slowing of the blood leakage so the body's natural clotting mechanisms can eventually take over and stop the blood flow. In hemodialysis, it is not uncommon to use five or six successive gauze compressions over a period of 20-30 minutes until hemostasis is achieved.

The prior art also discloses non absorbent materials to stop cannulation site bleeding. One way of accomplishing this was proposed in McRae et al. U.S. Pat. No. 4,233,980, where a pressure bladder made of flexible, non-elastic material and carried on a rigid, floor mounted arm is pressed against a site to produce hemostasis after an arterial puncture. Another way was proposed in Stanulis U.S. Pat. No. 4,182,338 where a skin contacting surface as soft as 25 Shore A durometer is part of a strap arrangement around the portion of the body where blood loss is to be prevented by compression of the skin contacting surface. Another way is Roth U.S. Pat. No. 5,263,965 which comprises a rigid disc as a manual compression aid.

Another significant problem with hollow bore needle cannulation is cannulation-induced infection to the cannulation tract and/or vessel. Although the needle is sterilized at the time of manufacture, and is maintained sterile in its package, needles may become unsterile as soon as its sterility protector is removed. At this stage it is susceptible to being contaminated by touch or air-borne bacteria. Or, the act of cannulation may drag into subcutaneous tissues bacteria from the skin surface or near-surface dermal layers. While the skin is disinfected with various chemicals, this is typically a relative rather than absolute disinfection, and bacteria will dwell on, or just under, the dead layer of skin cells of the cannulation site. It is known in the field of thoracic surgery to control infection induced by scalpels and the like, by laying over the disinfected skin area intended for surgical cutting a sheet of sterile plastic. This sheet is pressed against the skin, to which it adheres without adhesive. Not only is the outer surface of the sheet a sterile field on which surgical instruments may be placed without contamination, but the sheet's adherence to the skin tends to immobilize bacteria on the skin and under the dead skin cells. Owing to the clarity of the film, it is possible for the surgeon to visualize the cutting area and cut through the film as he/she surgically cuts the patient. Thus, no or few bacteria are dragged into the surgical site during cutting due to the effect of the sterile sheet. Tegaderm is a brand name of this prior art product.

Besides cannulating patients, needles also cannulate injection sites carried on medical devices, such as tube sets, drug vials, IV bags and the like. The prior art injection sites all comprise elastomeric bungs of a hardness not less than about 10 Shore A durometer, and are carried in typically plastic housings that hold the bung fixed and under compressive forces both for sealing the space between the bung and the housing, but also to urge shut the slit caused by a cannulating needle, when removed. Many elastomers are not suitable for injection sites because they either are either cored out when cannulated with a sharp, beveled hollow bore needle, or they leak through the cannulated slit even in the presence of the compressive forces urged on it by the housing. It has not been known until now of a resealable, non-coring elastomeric material that did not require a compressive or retentive rigid housing to be effectively resealable after passage and removal of needles, including hollow bore sharp needles.

Another problem of injection sites is that they must be manufactured into the medical device. For example a dialysis set typically comprises three or more injection sites at various locations on the set. Since many sites are never used during a particular medical procedure, the cost of manufacturing injection sites in every medical device, when only a few are used, represents a great monetary waste. It would be advantageous if a simple, cheap, attachable injection site to medical devices could be developed.

DESCRIPTION OF THE INVENTION

By this invention, a supersoft, typically elastomeric, pad or sheet is disclosed as an improved replacement for gauze squares, and other modes of achieving hemostasis on any bleeding site, whether by cannulation with needles of any size, or trauma from gunshot wounds and the like. Its action is the same. The typically substantially nonporous-surfaced pad stops the bleeding and promotes clotting, being a solid, pore free pad, or a porous pad typically having at least one, nonporous, skin like surface. The nonporous, skin like surface lies against the bleeding site, for hemostasis. The pores, if present, may be closed cells, or interconnected, open cells if desired, to contribute to softness of the pad. "Pores" are spaces in the pad which are large enough to pass blood or other medical fluid. The pad may be provided in a package in medically clean, or preferably sterile, condition. The pad may, in some embodiments, comprise a pair of opposed, parallel, equally sized major faces, forming a flat sheet, for simplicity of manufacture.

In the case of cannulation with a needle or catheter, the pad is placed against the cannulation site either before or immediately after the cannula is removed, and improves on gauze in two major ways. First, it is not absorbent of blood from the bleeding cannulation site, so much less blood is lost when it is pressed against the cannulation site to seal off the cannulation slit or hole. Second, because the supersoft elastomer can sealingly conform to even the micro nooks and crannies of the skin with extremely low or even essentially no applied force, which force can be applied manually, or by tape, or any appliance alone or in combination or in serial order, the vessel underlying the cannulation site is not likely to be damaged or pressed shut. Our lab tests show that after cannulating an in vitro vascular model with a 15 g needle and maintaining the fluid pressure within the vascular model at about 80 mmHg (the pressure of a strong hemodialysis graft access), a force of over 200 gms applied to gauze squares over the (now-removed 15G needle) cannulation site incision slows, but does not stop fluid flow out of the cannulation site, thus mimicking clinical experience with gauze. But by using a pad of super-soft elastomer of a durometer of no more than about 50 Shore 00, and preferably less than about 30 Shore 00, we were able to absolutely stop flow immediately from the cannulation site with only an applied holding pressure of about 25 gms. Because of the delicate nature of fistulae and grafts, and their tendency to stenose, such reduced force and immediate cessation of bleeding is a great advance. The supersoft elastomers conformal nature at low forces gives it great advantage as a pad, to be manually held and applied to a cannulation site and to be clear (transparent) for direct visualization of the bleeding site underneath the pad without having to remove the pad, as is the case with the prior art. There is a risk in the prior art of removing an opaque, hemostasis appliance before full clotting is attained, causing unnecessary blood loss from the patient.

Durometer measurements made herein are in accordance with ASTM Durometer Hardness Standard D2240-03.

Preferably, the pad may be supplied sterile.

The pad may be large enough to cover any size wound. For example, in the case of gunshot wounds or military trauma, the wound may exceed many square inches in bleeding area. Blood loss from such wounds can be so rapid that bleeding must be stopped prior to evacuating a patient to a hospital. One method to do this is to pour a clotting agent directly into the wound, for example flaked chitosan. This agent soaks up blood and provides enhanced surface area for rapid clotting. However, the clotted chitosan is difficult and time consuming to remove, once the patient is in the hospital, and the clotted blood within the chitosan is not available for harvesting by any one of the known, autologous transfusion methods. It is therefore an advantage for a large wound to be covered by a sheet of the material used in this invention, as its supersoft nature conforms to the nooks and crannies of the skin and the wound boundaries, requiring little or no applied pressure to seal against blood loss, and retaining blood which may be harvested later and returned to the vascular system. Sheets or pads of this invention can be applied within the body or wound to seal off bleeding arteries or vessels directly, so as to limit or stop internal bleeding. Because the sheet is preferably clear and self-sealing, medical workers can pass medical instruments through the sheeting without removing it.

This invention relates to a particular form of elastomeric pad which may be adhered (applied) to the skin of a patient or to the exterior of a medical device (such as a tube or bag wall) at a desired cannulation site, either prior to or after the actual injection. In some embodiments, the elastomeric pad may be clear, soft and thin enough, typically on the order of 2 to 5 or 7 millimeters, so that the cannulation site of a patient may be palpitated through the already in-place pad prior to cannulation, in order to find an underlying vessel or medical device by touch so as to maintain the sterility of the patient's intended cannulation site. The elastomeric pad may be coated with disinfectant, or it may be applied to pre-disinfected skin, or alternatively, to a wall of a medical device such as a solution bag or tubing, before cannulation, or applied after withdrawal of the cannula to prevent bleeding without necessarily continuing applied, strong external pressure.

Upon cannulation, an advancing needle or catheter can if desired pass first through the elastomeric pad, and then into the skin of the patient or material of the medical device, typically into a vascular system of the patient or lumen of the medical device. Upon withdrawal of the cannula, the pad exhibits the surprising property of resealing without a compressive housing, and provides significant suppression of bleeding or fluid leakage, with a consequent increase of hemostasis in a patient (or suppression of leakage from the medical device), with significantly less need for compression to facilitate the hemostasis. Also, the cannulation site on the skin (or medical device) may be subjected to anti-microbial effect due to the presence of an antiseptic at the junction between the pad and the skin or medical device. Many suitable anti-microbial antiseptics are quite volatile, and the pad of this invention provides a physical barrier that increases the term of active disinfection by reducing the evaporation rate of the antiseptic material, such as alcohol. Pores in the pad, if any, can be used to store antiseptic, thus extending the contact time of the antiseptic around the wound as it diffuses through the pad material to the wound area. Bacteria on or within the skin or medical device may also be immobilized by the pad, and thus prevented from being drawn in through the skin or medical device by the advancing cannula. Thus, aseptic conditions can be promoted during the time that the cannula resides in the skin. Also, hemostasis with less or even virtually no added pressure can be achieved after withdrawal of the cannula. Then, the elastomeric pad can be removed when hemostasis has fully taken place, and when it can be expected that there will be no further spontaneous bleeding.

Thus, reduction of blood loss can be achieved, particularly in the situation of chronic patients, where access to the vascular system must take place frequently. This invention can also work with fresh cannulation sites or repeat cannulation sites, commonly known as "buttonhole" sites.

Accordingly, a method is provided which comprises the method of suppressing bleeding through the skin of a patient which comprises: applying to the skin of the patient a soft pad of typically elastomeric material having a hardness of no more than about durometer 50 Shore 00 to suppress the bleeding. Resealability of the pad to a needle puncture may be provided if the soft pad is an elastomeric material. However, soft (no more than about Durometer 50 Shore 00), non-elastomeric materials such as polyethylene foam pads may be used for effective bleeding suppression in those circumstances where a needle puncture is not used. The elastomer or non-elastomer pad used may either be a solid, pore free pad, or a porous pad typically having at least one, non-porous, skin-like surface, unless the material of the pad is of blood repellant material or the pores are small enough so that blood does not substantially enter into them, or the pores are separated as in a closed-cell foam, so that the pores may be used to impart softness to the pad, without significant seepage of blood through the pad.

Typically, materials as soft as or softer than Durometer 30 Shore 00 may be used with good effect.

The soft pad may have a non-porous surface for abutting the skin or a wall of a medical fluid container which has the required hardness of no more than about Durometer 50 Shore 00. Optionally, other portions of the pad may be harder, to provide support and the like.

If desired, after the soft pad is applied, one may pass a medical needle through the elastomeric pad into the tissue of the patient, and thereafter withdraw the needle with substantially suppressed bleeding.

In this circumstance, in some embodiments the elastomeric material of the pad may have a hardness of no more than about durometer 30 Shore 00, for example 10 Shore 00 or less.

Alternatively, the needle or hollow cannula may be inserted through a point of the skin of the patient, and, thereafter, the soft, pad described above may be placed on the skin of the patient to cover the point of the skin through which the cannula penetrates. Thereafter, the cannula or needle is removed.

Also, a soft, elastomeric pad described above may be applied to the wall of a hollow medical device such as a plastic solution bag. One then passes a medical needle through the pad and the wall of the hollow medical device, and thereafter withdraws the needle, with leakage through the hole formed in the wall by the needle being suppressed. Here also in some embodiments the elastomeric material of the pad may have a hardness of no more than about durometer 30 Shore 00, for example 10 Shore 00 or less.

An "elastomer" is defined as a rubbery material having at least one hundred percent elongation to break, and which snaps back to substantially its original configuration when released from stretching, like rubber. An elastomer is not a gel, which has little or no ability to snap back toward an original configuration after stretching.

Further, in accordance with this invention, a method is provided which comprises the step of: applying a pad to the skin of a patient or a medical device, the pad consisting essentially of an elastomer or other flexible material having a hardness of no more than essentially durometer 50 Shore 00 and preferably no more than durometer 30 Shore 00. Wounds can thus be sealed to stop bleeding, and, similarly, puncture leakage in a medical device can also be stopped.

The material of the pad preferably has a high elongation to break, typically at least about 500% or preferably about 900% to 1000% or more. Such an elastomer exhibits high resealability, so that the needle puncture hole does not readily leak blood at natural blood pressures, particularly from an artery, vein, or fistula, optionally without a compressive or retentive housing as in the prior art of injection sites carried on medical tube sets. Also, the elastomeric material, although very soft, tends to be non-coring to conventional medical needles. Thus, a stick—on injection site may be provided by this invention.

In some embodiments, the elastomer pad has a thickness of about 0.1-0.5 cm., and has a hardness of no more than about 50 Shore 00 durometer, and preferably no more than 30 Shore 00, the elastomer material being non flowable.

In some embodiments, the elastomers of this invention comprise an oil plasticized material such as an oil-plasticized block copolymer comprising (A) at least one crystalline, aryl-containing polymer segment, and (B) at least one elastomeric, aliphatic polymer segment. Some plasticized elastomers of this type are disclosed in U.S. Pat. No. 5,508,334 of John Y. Chen, and numerous other patents by the same inventor, and also in U.S. Pat. No. 5,994,450 of Tony M. Pearce, the disclosures of which are incorporated by reference herein.

In some embodiments, the crystalline, aryl-containing polymer segment comprises monoalkenylarylene polymer units such as styrene or alphamethylstyrene. The elastomeric, aliphatic polymer segment may consist essentially of isoprene and butadiene polymer units in some embodiments.

The pad so used may be coated on one side with a skin adhesive and directly adhered to the skin, so that preferably the exterior of the pad has no adhesive. Or an adhesive may be mixed into the material, or be a basic attribute of the tacky material. However, in other embodiments, the pad may be carried under a cloth, or a non-woven fabric or plastic strip, or a length of adhesive tape as in a "Bandaid" ™ arrangement, the elastomer pad being a replacement for the gauze pad of a "Bandaid" dressing. The strip may preferably carry a hole, thus exposing the pad, which may be transparent, where cannulation is intended. The pad may be carried in or on a single sheet or within a multi-sheet envelope, which envelope also may comprise plastic sheeting, for example, thermoplastic sheets of polyethylene, pvc, polyurethane, or similar materials, particularly when the adhesive desired is not compatible with, or does not adhere well to the elastomeric pad. The sheet or envelope carries the skin adhesive on one side thereof to adhere the pad to the skin of the patient. The pad may be at least partially melted so the material entwines with a cloth or non-woven or plastic material adhered to a strip. Preferably the pad will not detach from the skin or medical device until desired. Preferably this adherent, adhesive device will prevent leakage from the cannulation site between the skin (or medical device) and the pad, when the needle has been removed.

As stated above, in some embodiments, the envelope, when used, may define a central opening to expose the pad carried therein. For example, the envelope may have a pair of opposed, major faces, with each face defining a central opening, typically aligned with each other, to expose the pad carried therein.

Some embodiments of the materials used as plasticized elastomers may comprise a high viscosity poly (styrene-ethylene-butylene-styrene) triblock copolymer having styrene end blocks and ethylene and butylene center blocks in a ratio preferably within a range of about 20:80 to about 40:60, as described in Chen U.S. Pat. No. 5,508,334, column 5. The polymer, when blended in a melt with an appropriate amount of plasticizing oil, may comprise a gelatinous elastomer composition having in some embodiments a relatively high elongation to break of at least about 1600%, and a tear resistance of at least about 300,000 or 500,000 dynes per centimeter, with substantially complete, rubbery snap back when extended to about 1200% elongation, as called for in the cited Chen patent. Ultimate tensile strength may in some embodiments be at least about 800,000 dynes per square centimeter, having a low elongation set at break of substantially not greater than about two percent.

Other suitable materials are Versaflex CL2003x thermoplastic elastomer, sold by GLS Corporation of McHenry, Ill., and Dermasol DS309 of California Medical Innovations, of Pomona, Calif.

Alternatively, silicone or polyurethane formulations of the proper softness, with or without plasticizers, may be used.

Surprisingly, it has been found that many of the materials of the above-cited patents, and other soft materials, exhibit excellent and unexpected hemostatic or leak resistance characteristics when adhered to an injection location such as a patient's skin or a medical device, with the added advantage that needle coring is suppressed by these materials, despite their softness and resealing of the needle slit despite lacking a compressive housing.

Further in accordance with this invention, a pad of elastomeric material for hemostasis may be provided, the pad having a softness of no more than about durometer 50 Shore 00. The pad further defines, in some embodiments, at least one and preferably a pair of integral retention straps, which are made of the elastomeric material and which form one piece with the pad, being typically co-molded with the pad. The thickness of the pad is in some embodiments at least twice, and typically three or more times, the thickness of the retention straps.

It is preferred for the hardness of the elastomeric material to be no more than about durometer 30 Shore 00, and for the elastomer to have an elongation to break of at least about 500%.

Such a pad with straps may be used for hemostasis by wrapping the pad around the arm or leg of a patient, overlapping the retention straps along a portion of their length. As they wrap around the arm or leg, this overlapping may take place at any circumferential point on the arm or leg spaced from the location of the pad. Typically this overlapping takes place at a diametrically opposed area of the arm or leg from the location of the pad. Thus, the pad can be retained in position on the skin of the patient by natural tack adhesion between the retention strips. In that position, the pad may provide hemostasis to a cannulation site of a freshly withdrawn needle or catheter, and may be retained in position for as long as necessary while providing only a little degree of compression, and effecting good hemostasis while preventing bleeding from the hole in the patient's tissue left behind by the needle or catheter. This hemostasis can even be effective to cause hemostasis in catheter access sites where connection has been made to an artery.

Further in accordance with this invention, a method comprises: inserting a hollow cannula through the point in the skin of a patient and into a blood vessel; thereafter placing a soft, elastomeric pad on the skin of the patient to cover the point of the skin through which the cannula penetrates; and thereafter removing the cannula. The pad in question is as described above, having a hardness of no more than about durometer 50 Shore 00, and typically less than 30 Shore 00, whereby bleeding is suppressed by the pad. This method greatly facilitates the prevention of bleeding upon withdrawal of the hollow cannula from the blood vessel, in that, while insertion of the cannula into the blood vessel can be done conventionally, the pad of this invention can then be placed over the skin of the patient at the point of cannula penetration, and the high resilience and softness of the elastomeric pad can immediately suppress bleeding upon withdrawal of the cannula, without any significant bleeding taking place while the pad is being applied after removal of the cannula.

The soft, elastomeric pad may be affixed to the skin of the patient using preferably substantially transparent tape.

Furthermore, advantageously, in some embodiments the pad may be of a solid, domed shape. The term "dome" or "domed" implies an elastomeric structure having a rounded, convex, outer surface, in which a central portion of the elastomeric pad is substantially thicker than peripheral portions. Specifically, the central portion may be at least twice as thick as the peripheral portion of the pad at the edge of the pad. The edge of the pad may have a thickness tapering to essentially zero, or it may connect to an integral strap or outer flange.

The pad of this invention, for example the pad of solid, domed shape described above, may reside in a recess defined by a wall of a plastic sheet. The sheet also has a flat flange at least partly surrounding the recess, with the flat flange being affixed to the skin of a patient with tape, adhesive, or the like, and with the recess wall and the patient's skin together enclosing the soft, elastomeric pad, while the pad abuts the skin. The plastic sheet wall with its recess may comprise a container which is manufactured in a manner similar to known, single-serving jelly containers used in restaurants, and in which a flat flange surrounding the recess may be covered with a peel sheet which is manually removable, in the manner of a single-serving jelly container. Also, the flat flange may be affixed to the skin through an adhesive layer carried on the flange.

The plastic sheet may be made of poly(ethylene-vinyl acetate), or any other desired plastic material. The recess (such as a dome-shaped recess), may be cold formed in the plastic sheet.

Furthermore, as described previously, the hardness of the elastomer may preferably be no more than about durometer 30 Shore 00, while the elongation to break for the elastomer may preferably be at least about 800 percent, and the tear resistance may in some embodiments be at least one million dynes per cm. Also, the elastomeric pad may have a glass—smooth, flat face, which may be placed in contact with the skin.

The lower limit of hardness for an elastomer that may be used in a practical manner in accordance with this invention varies to an extent depending upon the pressure of blood (or fluid in a medical container). Higher pressure fluids generally are better sealed with an elastomer which has a hardness that is somewhat greater than may be required in the circumstance where fluid pressures are lower, although by this invention the hardness is no more than about 50 Shore 00 in any circumstance, relating to sealing of blood pressure and of the walls of medical fluid containers. For example, a somewhat softer material can desirably be used for the sealing of a venous puncture than may be required for the sealing of an arterial puncture.

In some embodiments, the elastomeric pad may slightly overfill the recess in the plastic sheet, so that an outer portion thereof projects beyond the plastic sheet, to provide firm contact with the skin, particularly when the elastomeric pad is placed in contact with the skin without removal from the recess of the plastic sheet, to assure good skin contact. Alternatively, the elastomeric pad may be removed from the recess for use.

Thus, bleeding may be effectively controlled by applying the typically elastomeric pad of this invention to a wound, such as at the point where a cannula is inserted through the skin, using, in some embodiments, a soft pad of elastomeric material having a hardness of no more than durometer 50 Shore 00, with the pad being of solid, dome shape with a flat bottom.

DESCRIPTION OF SPECIFIC EMBODIMENTS

Figure 1:
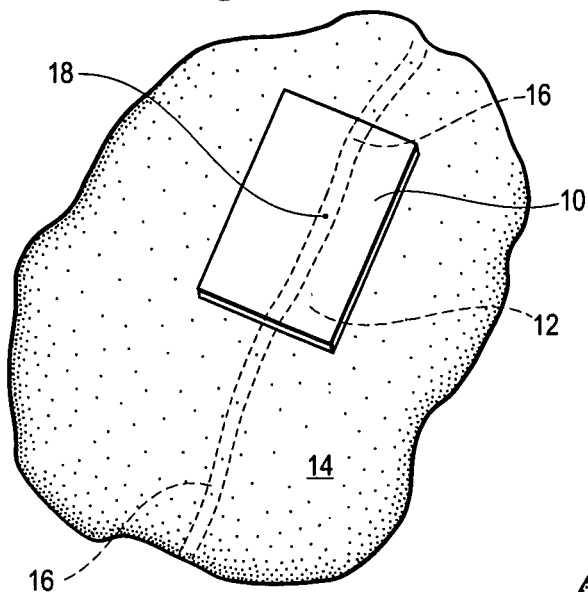
FIG. 1 is a perspective view of a pad of an embodiment of this invention.

Referring to FIG. 1, a pore-free pad of very soft elastomer 10 is shown, preferably having a coating of adhesive 12 on its lower face for adhesion to the skin. Pad 10 has a softness of less than durometer 30 Shore 00. It can be manufactured in accordance with the teachings of Pearce U.S. Pat. No. 5,994,450, for example comprising a polystyrene-hydrogenated poly (isoprene and butadiene)-polystyrene copolymer, plasticized with either mineral oil or a combination of mineral oil and resin. Other suitable materials for manufacture of the pad of this invention are manufactured, for example, by Edizone, LC, a Utah Limited Liability Company of Pleasant Grove, Utah. Other suitable materials may comprise, for example DS309 Dermasol, manufactured by California Medical Innovations of Pomona, Calif. Typically, the softness (hardness) of materials used for the pad 10 may be no more than about durometer 60 Shore 000, all according to tests according to the ASTM Durometer Hardness Standard D2240-03, and they may even be so soft as to not register on the Shore 00 scale and registrable only on an extremely soft scale according to a "gram bloom" test or the Shore 000 scale. Gram bloom involves the applied force necessary to depress a 10 mm diameter flat probe 4 mm into a sample of elastomer.

It is also sometimes desirable for the material used in this invention to have a tear strength of at least about 800,000 dynes per cm, and an elongation to break of said elastomer of at least about 900%.

Pad 10 may be adhered to the skin 14 of a patient, after the skin has been wiped with an antiseptic such as povidone iodine or an alcohol such as isopropanol. The pad may be applied while the antiseptic is still present on the skin, so as to trap the antiseptic against the skin. Any appropriate antiseptic may be used, and the antiseptic may be carried on or in pad 10, if desired. An increased-viscosity or gelled antiseptic may also be used, for example the antiseptic of patent Publication No. US 2003-0175323 A1.

Pad 10 may be of any desired dimension in length and width, blanket size to button size, and may be of rectangular shape, or nonrectangular shape, such as circular or oval, if desired. It may have a thickness of about 0.2-0.3 cm, which may be thin enough to feel the presence of a vein 16 through pad 10 by means of finger touch, because of the extreme softness of the elastomer material of pad 10. Then, a needle may be inserted in normal manner through pad 10 to penetrate vein 16 for a conventional IV injection process, which may include large volumes of parenteral solution, blood collection, or extracorporeal blood processing, with the needle penetrating pad 10 at point 18. Pad 10 is desirably substantially transparent for visualization of the skin underneath.

When the needle is withdrawn, point 18 recloses, and substantially reseals to prevent leakage of blood out of vein 16. Furthermore, such ultra soft material, preferably of relatively high tear resistance (tear strength of over two million dynes) and relatively high elongation to break, is resistant to coring by an injection needle, so that hole 18 recloses and reseals, optionally with gentle manual pressure, to an extent sufficient to prevent pressurized blood (or other fluid) leakage through hole 18. Also, because of the adhesive attachment of pad 10, little blood leaks transversely from the puncture hole in the skin laterally between the skin and the adhering material of pad 10.

Alternatively, pad 10 may be applied immediately after withdrawing of a needle (or catheter) that penetrates the skin, such as a fistula needle, to suppress bleeding. For example, in hemodialysis and other extracorporeal blood treatment procedures, when a fistula needle is withdrawn from the patient, substantial bleeding takes place because of the larger diameter of fistula needles (and similarly with certain other extracorporeal blood flow access needles or catheters). Thus, as previously described herein, it is normal that special procedures for suppressing bleeding must take place when those needles and catheters are withdrawn. By this invention, pad 10 can be used to avoid those previously-necessary special procedures as described above, while also resulting in reduced blood loss.

The pad 10 of this invention may be of a small, button-like size of about one to six centimeters diameter or the like, particularly when it is desired to suppress the bleeding after withdrawal of a needlelike cannula, whether or not the pad is applied before penetration of the cannula, or after the cannula has been withdrawn. Also, pad 10 may be used to seal larger, laparoscopic catheter holes in a patient, or holes which are formed in arterial walls by cardiac angiography catheters, angioplasty catheters, electronic mapping or ablation catheters, and all other medical devices which cause bleeding when they are withdrawn. A current, recommended procedure for the suppression of bleeding after the withdrawal of catheters and the like from the vascular system is pressure with the use of a sandbag for about three hours. The pad of this invention may serve as a substitute for this, being firmly applied to the resulting wound after withdrawal of a catheter, blocking bleeding, but permitting the patient to be mobile, and suppressing, or preferably completely eliminating, bleeding.

Instead of using adhesive 12, pad 10 may be applied to the patient in any desired, conventional manner including adhesive tape, a conventional clamp, a tie around an arm or a leg, or even manually, if that is appropriate.

Furthermore if desired, pad 10 may comprise a relatively large mat or blanket of the soft elastomer material, optionally being thicker than specific thicknesses recommended for other uses above, for example a thickness of about 0.5 cm or greater, and a length and width each of at least about 10 cm, to provide a bleeding suppression blanket, to suppress bleeding from larger wounds such as bullet and knife wounds, or other severe lacerations, providing a mode of first aid to suppress external bleeding of an injured patient. The weight of a thicker blanket of the material of this invention can provide sealing force without the need for added application of pressure, although such added pressure may of course be applied by any desired means, such as tying the pad to the patient, or the use of weights or manual pressure. Furthermore, such a form of pad 10, being of relatively greater thickness, such as a thickness of 1-5 cm. and being of pillow-case or blanket size, can be prewarmed, to provide a bleeding suppression blanket that can wrap the patient in whole or in part, and also addresses the issue of shock by providing positive warmth to the patient. Also, a hot water chamber may be provided in the pad, like a form of hot water bottle.

Also, when pad 10 is in the form of a thick blanket for bleeding suppression, it may carry an adhesive on one side for direct adhesion to the skin of the patient, with the adhesive providing further suppression of bleeding and migration of blood between pad 10 and the skin, or its natural tack may be used to retain the pad blanket 10 on the skin.

Furthermore, pad 10, in all its forms, tends to cause the clotting to take place directly in the needle track or the other injury, with the result that there are fewer bacteria in the scab which forms, and opens the possibility of less scarring.

Vitamin E oil and/or another anti-scarring agent or other medicament may be added to elastomer formulation of this invention, for release to the skin surrounding the injury, and the injury itself, such as the needle track. Also, other medicaments may be provided to the formulation of pad 10, either as a separate layer, or integrally mixed within the material of the pad itself. For example, clotting agents may be added to promote clotting, such as collagen.

The material of this invention may contain other agents as well, for example, clotting (hemostatic) agents such as collagen and other known materials, including simple, inorganic salts and other promoters for blood clotting particularly outside of the body. Other examples of possible clotting agents include: Aluminum Ammonium Sulfate, Aluminum Potassium Sulfate. Chitosan, Epinephrine, (1:50,000-1:1,000), Tannic Acid, Collagen, Styptic Collodion, Hyaluronic Acid, Sodium Hyaluronate, Aluminum Sulfate, Cotarine, Cotarine Chloride, and Cotaminium Chloride.

In some embodiments, the surface of solid, nonporous pad 10 which faces the skin (or any other surface which is being sealed) may be glass-smooth, to promote engagement of the ultra soft pad material with irregularities in the skin or other surface, to promote sealing and to prevent the flow of blood or other fluid from the hole being sealed laterally between the pad and the skin or other surface.

Remarkably, it has been found that the materials of which pad 10 can be made as described herein generally do not need to be substantially compressed to reseal from needle sticks. Thus, while they may be used in a housing, they do not require a housing in many uses, and a housing in which they are contained does not have to hold them under compression to obtain desirable results, although such compression may be used if desired.

The shape of pad 10 of course is not limited: it may comprise a round button, or a rectangular one of diameter or other transverse dimension of one or more centimeters, or, as stated above, it may comprise a large blanket of appropriate size to address severe lacerations, and to at least partially wrap the patient, being heated if desired to address shock while also suppressing external bleeding.

Accordingly, a stick-on injection site and/or hemostasis site is provided, which can be applied when an injection is required, and which facilitates aseptic conditions, reducing the drawing of bacteria into the body as the cannula advances through the skin, and providing good hemostasis at normal blood pressures.

Alternatively, skin 14 could be a wall of a plastic solution container, a plastic tube, or the like, with the same sealing characteristic being achieved, providing a penetrable injection site for a needle.

Figure 2:
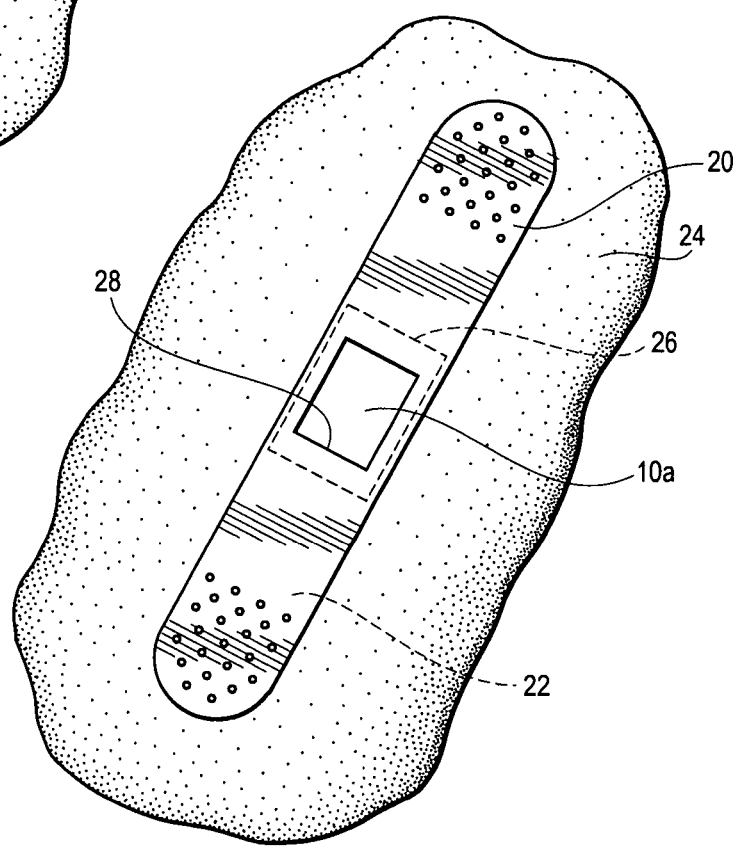
FIG. 2 is a plan view of a pad of an embodiment of this invention, carried on an adhesive coated sheet of plastic.

Turning to FIG. 2, pad 10a, similar to pad 10, is carried on an adhesive plastic strip 20, with adhesive layer 22 on at least a portion of the underside of strip 20 permitting adherence as shown of strip 20 and pad 10a to the skin 24 of a patient, which alternatively may comprise the wall of a solution bag, or an apertured tubing wall over which pad 10a extends, or the like. Plastic strip 20 can carry adhesive to adhere to the skin or wall 24. Also, the periphery 26 of pad 10a can adhere to the same or a different kind of adhesive carried on the underside of plastic strip 20 to position pad 10a in fixed manner covering an aperture 28 formed in plastic strip 20.

Figure 3:
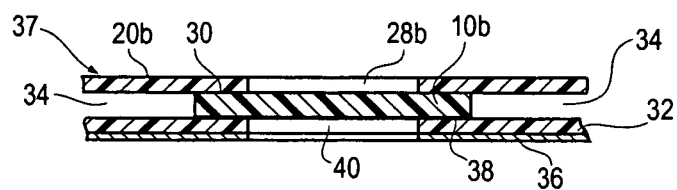
FIG. 3 is a transverse sectional view showing the pad of an embodiment of this invention secured in an envelope defined by a pad of plastic sheets, which are normally peripherally secured together, but shown in separated fashion for clarity, forming an envelope which contains the pad of this invention.

Alternatively, FIG. 3 shows an embodiment that looks substantially identical in plan view to the embodiment of FIG. 2, in which an elastomeric pad 10b is attached to plastic strip 20b and retained there by a peripheral adhesive 30. Also, an optional, additional plastic strip 32 may serve to form an enclosing envelope by a peripheral seal with plastic strip 20b, enclosing elastomeric pad 10b. Such seals may be peripheral seals at areas 34. Bottom plastic strip 32 may carry an adhesive layer 36 for adhesion to the skin and an upper, peripheral adhesive layer 38 for retention and positioning of pad 10b within the envelope 37 defined between plastic strips 20b and 36.

Preferably, each plastic strip defines an aperture 28b, 40 to expose both sides of pad 10b. Pad 10b, carried within its envelope 37, is exposed for finger palpitation to find a blood vessel under the skin in the case where adhesion to the skin is desired, and generally for open needle access through pad 10b and the wall or patient's skin to which it is adhered by means of the envelope 37.

Generally, upon withdrawal of a needle, the puncture which is formed in the respective pads 10, 10a, 10b reseals without significant compression because of the unique physical characteristics of the material used as the elastomer.

A specific example of silicone material which may be used to form the pad of this invention is Rhodia 40022 reinforced silicone gel. Softer silicones than this material may also be used, if they retain the characteristics of a nonflowing elastomer.

Alternatively, pad 10 may be applied or adhered to the skin by conventional taping, with the center of the pad left exposed for needle penetration, so that an adhesive layer 12 is not needed. The natural tack of pad 10 may provide some skin adhesion to seal against blood flow.

When the elastomeric material is plasticized with a (preferably metabolizable) lubricating oil, it may be possible to cannulate through the pads 10, 10a, 10b with a non-siliconized needle, in which the needle picks up enough lubricant from the disk to desirably reduce the force of cannulation in a manner comparable with a siliconized needle, to avoid the use of siliconized needles.

As an additional feature, pads 10, 10a, 10b may contain enough impregnated antiseptic, one such example being isopropanol, so that the inner surface of the pad, lying against the skin, will have an alcohol content sufficient for continuing antimicrobial effect. Alternatively, a layer of an alcohol-containing gel may be preapplied to the skin 14, and then pad 10 may be applied to the skin and, if desired, taped in position to provide a stick-on injection site. Such alcohol-containing gels are described in Utterberg U.S. Patent Publication US 2003/0175323 A1. Or, a porous pad with a solid skin can have the pores filled with alcohol or another antimicrobial agent, for continued antibacterial effect.

Figure 4:
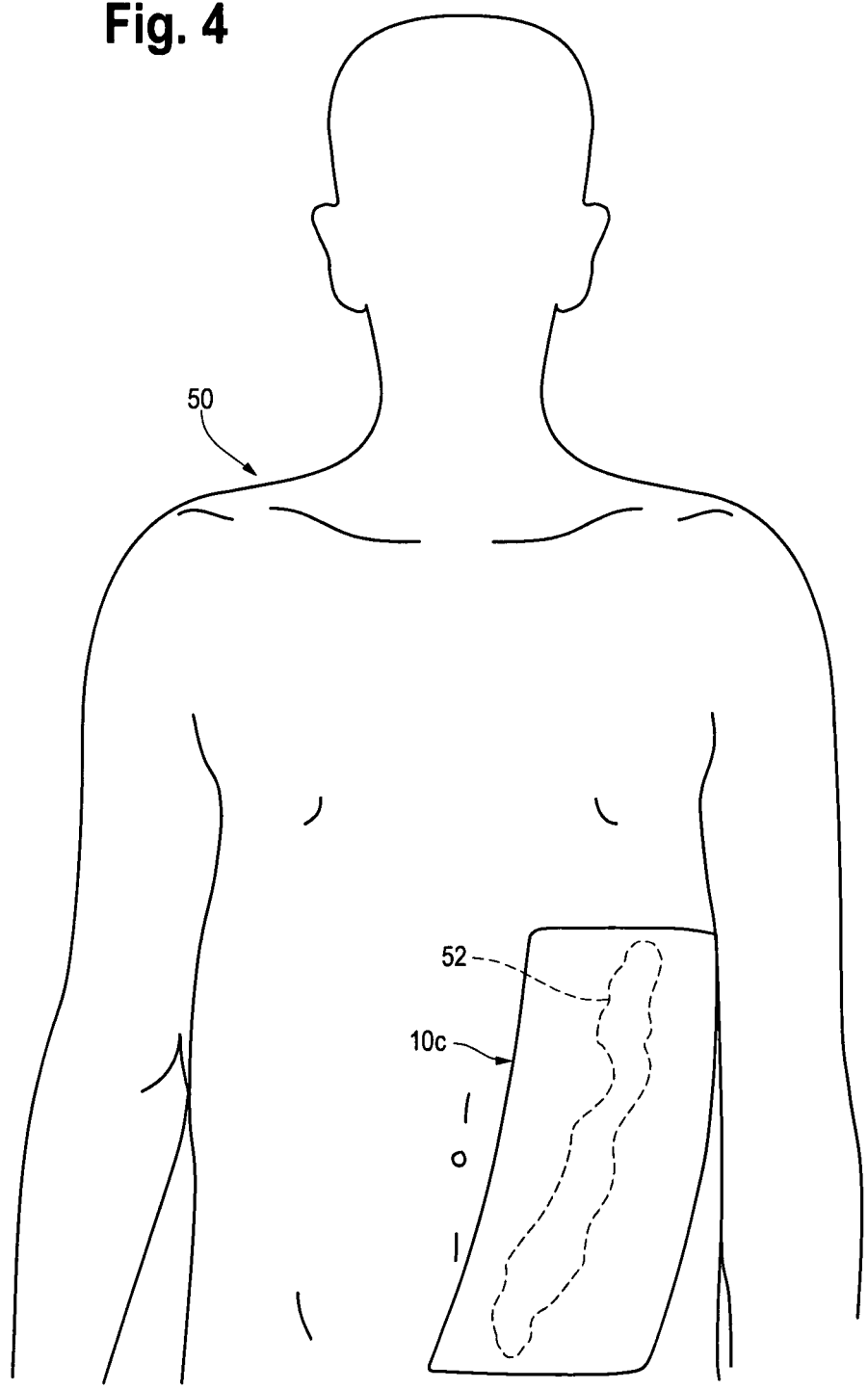
FIG. 4. is a perspective view of a pad of an embodiment of this invention placed over a large trauma wound.

Referring to FIG. 4, a patient 50 who has suffered a severe laceration 52 may be treated by immediate care personnel in the field by simply closing the laceration and covering it with an enlarged pad 10c made in accordance with this invention. Pad 10c may comprise a soft, transparent elastomer material as described above. A specific material used for pad 10c and other pads may be Dermasol DS309, comprising a styrene-ethylene/butylene-styrene copolymer which carries more than 50% of mineral oil as a plasticizer. The particular DS309 material has a durometer of about 20-30 Shore 000, an ultimate elongation (elongation to break) of about other pads in accordance with this invention) may comprise 15-20% of styrene-ethylene/butylene-styrene copolymer; 80-85% of mineral oil USP; 0.1-0.3% of antioxidant; and 4 parts/per million/of Vitamin E, this being a formulation published for Dermasol by California Medical Innovations.

Pad 10c may be of any appropriate shape or size, and may have any desired thickness, for example, from 0.2 cm. to 1 cm. Pad 10c has a natural tack so that, if desired, it can spontaneously be retained over the wound site 52. Alternatively, it may be held by tape or straps, as desired, to hold blood in the wound site and to promote hemostasis (clotting). If desired, a hemostasis (clotting) agent as described above may be applied, or such a hemostasis agent may be carried as a layer on the inner face of pad 10c, or may be an ingredient in the elastomer formulation of pad 10c to leak out into the wound to promote clotting.

Figure 5:
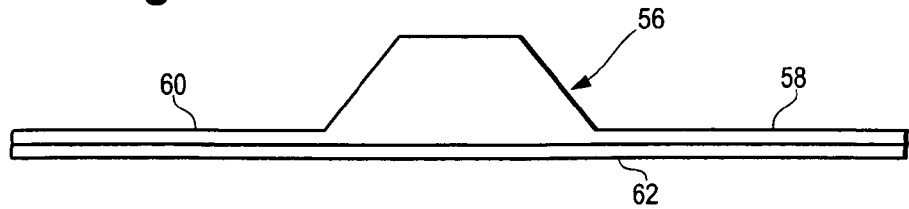
FIG. 5 is an elevational view of another embodiment of this invention, showing a pad with an integral strap.

Referring to FIG. 5, a pad 56 is shown, being made of an elastomeric material in accordance with this invention, such as Dermasol DS309, and further defining a pair of integral retention straps 58, 60 which are made of the same elastomeric material and which form one piece with the pad, having been preferably molded with the pad in a single step. The thickness of the pad 56 can be seen in this embodiment to be about five or six times greater than the thickness of the retention straps. Pad 56, with integral straps 58, 60, may be carried on a relatively stiff backing strip 62 for storage, from which it may be removed for use.

This pad may be used by being placed on an arm or leg of the patient over a needle or catheter injection site, before or after insertion and withdrawal of the needle or a catheter introducer device. Then, after withdrawal of the needle or catheter, pad 56 can reseal, to facilitate hemostasis, and also it prevents blood leakage.

Pad 56 can be attached by stretching the straps 58, 60 around the arm or leg of the patient, causing portions of the straps to overlap, typically at a diametrically opposed portion of the arm or leg from the position of the pad on the skin. The natural, adhesive tack of the straps can provide desired adhesion to each other, holding the pad in place on the arm or leg without added adhesive. Alternatively, an adhesive or other technique may be used to hold the straps in position.

Figure 6:
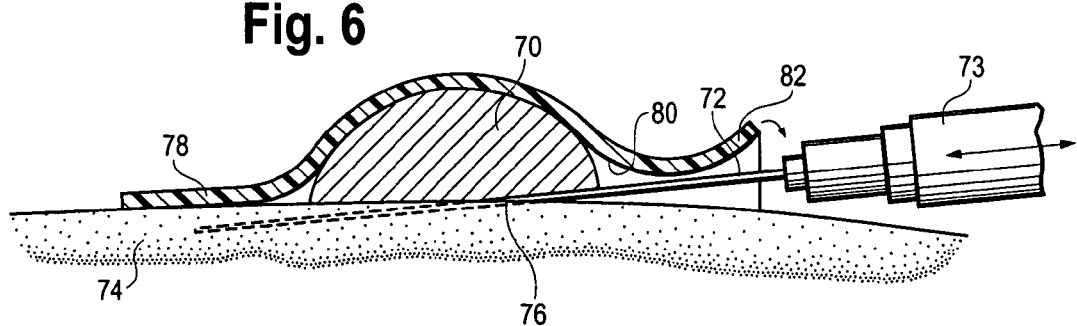
FIG. 6 is an elevational view, taken in section, showing a needle penetrating the skin, with a dome-shaped pad of this invention overlying the entrance point of the needle through the skin and secured there by an adhesive sheet member.
Figure 7:
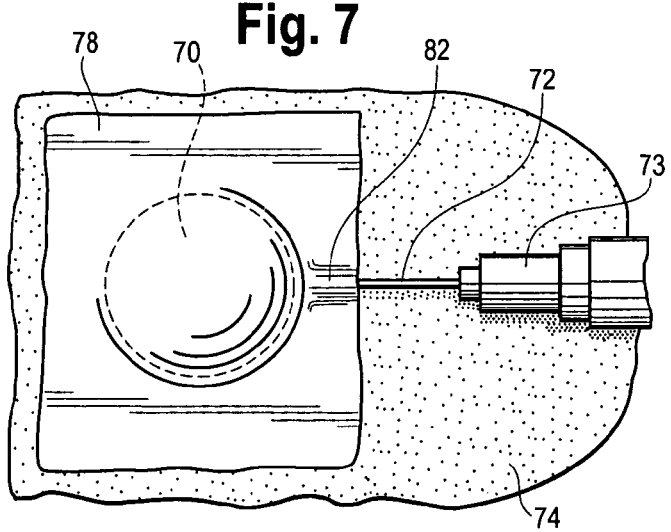
FIG. 7 is a plan view of FIG. 6.

Referring to FIGS. 6 and 7, a soft, elastomeric pad 70 is of dome shape, and is made of a soft, elastomeric material as described above, preferably having a Durometer of no more than about 50 Shore 00, and preferably no more than about Durometer 30 Shore 00.

In the embodiment shown in FIGS. 6 and 7, needle 72 penetrates the skin 74 at point 76, the needle being representative of any desired cannula used for obtaining access to the body including needles for access to the vascular system of the patient such as fistula needles. Alternatively, catheters may be used as desired and as discussed above.

In this particular embodiment, before needle 72 is withdrawn, domed pad 70 is laid over needle entrance point 76 of the needle into the skin of the patient. A rectangular cover sheet 78, having an inner-adhesive layer 80, overlies domed pad 70, as further illustrated in FIG. 7. Basically, sheet 78 is a rectangular section of adhesive tape or the like.

When a rectangular form of adhesive sheet 78 is provided as shown in FIG. 7, a portion 82 of the sheet around needle 72, carried by needle hub 73, may remain open as shown, particularly in FIG. 6, in the immediate area around the needle so that, after pad 70 has been placed over needle penetration point 76, needle 72 can be withdrawn, and the portion 82 of cover 78 may be manually pressed down onto the skin 74 to provide a seal of wound 76 caused by the needle and to suppress bleeding.

Figure 7A:
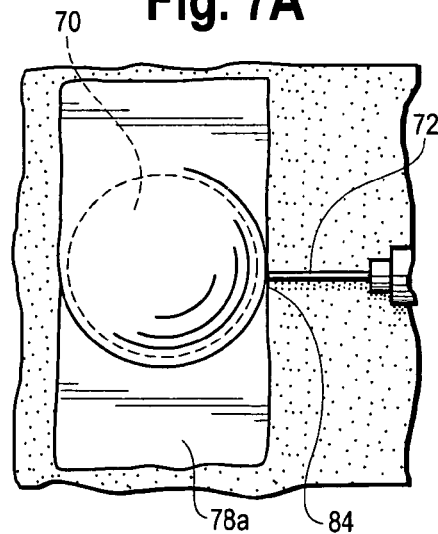
FIG. 7A is a modified version of FIG. 7.

Alternatively, as shown in FIG. 7A, elastomeric pad 70 may be laid down as shown in FIG. 6 over the wound 76 caused by needle 72, but with the cover sheet 78a overlying pad 70 being in the form of a narrower strip, so that at least one edge 84 of pad 70 is effectively laterally exposed, without interference by the adhesive tape cover 78a, so that needle withdrawal 72 is easier, and with less pain.

Other pads which are not of dome shape may also be used in this invention.

Figure 8:
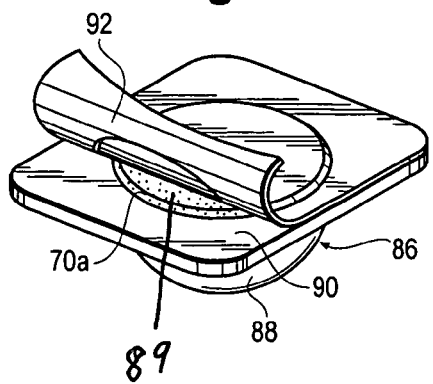
FIG. 8 is a perspective view of an elastomeric, dome-shaped pad, carried in a dome-shaped recess which is defined by a dome wall of a plastic sheet, which sheet also has a flat flange surrounding the dome wall, and showing a removable peel tab used to enclose the pad until use is required.
Figure 9:
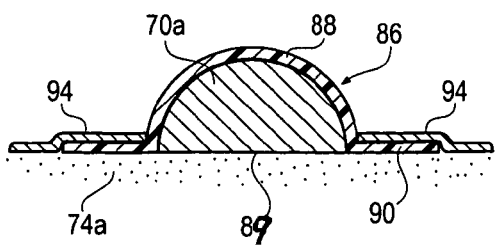
FIG. 9 is an inverted, sectional view, taken in elevation, of the dome-shaped elastomeric pad of FIG. 8, carried in the dome-shaped recess of the plastic sheet, and shown adhered to the skin of a patient, with the dome wall of the plastic sheet and the patient's skin together enclosing the soft, elastomeric pad.

Turning to FIGS. 8 and 9, an elastomeric pad 70a of dome shape can fit into a plastic housing 86, which is formed from a plastic sheet having a dome-shaped recess defined by a dome wall 88 of the plastic sheet, with the plastic sheet also defining a flat flange 90 surrounding dome wall 88. The dome wall and recess may also be of other shapes as desired.

A removable peel covering 92 may be conventionally applied to the plastic sheet package 86 to seal elastomeric pad 70a until the time of use.

The basic technology may be similar to that technology which is used to manufacture single serving jelly containers used in restaurants, except that, in this embodiment, the recess is dome shaped. However, other shapes for container 86 may be utilized, including the conventional shape of a restaurant jelly container. If desired, an adhesive may be placed on the outer face of flange 90, to facilitate connection with the skin.

If desired, after opening by peeling away covering 92, soft, elastomeric pad 70a may be removed and placed on the skin in the manner indicated in FIGS. 6 through 7a. Alternatively, elastomeric pad 70a may be retained in container 86 and placed on the skin 74a along with container 86, as illustrated in FIG. 9. If desired, elastomeric pad 70a may have a flat face 89 which is slightly elevated above the face of flange 90 when peel layer 92 is removed (as shown in FIG. 8) so that, when placed on the skin 74a as in FIG. 9, there may be a desirable, slight compression. This compression may be provided by adhesion of flange 90 to the skin or as shown, by the application of tape strips 94 to flange 90. Package 86 with its attached, soft, elastomeric pad 70a may be placed on the skin while a needle is penetrating to cover wound 76 or, alternatively, package 86 and/or pad 70a may be placed on the skin after withdrawal of the needle or other cannula, to cover the resulting wound left behind by the withdrawn needle or cannula. For example, a wound from an angioplasty catheter or the like may be covered by pads 70, 70a, or a hemodialysis needle wound may be covered by pads 70, 70a.

The plastic sheet of container 86 may be made of poly (ethylene-vinyl acetate) (called EVA), polyethylene, or the like. EVA bonds to desirable, plasticized materials that form pad 70a, and container 86 may carry adhesive for adhesion to the skin, and/or may provide a good connection with removable cover 92. Also, the poly(ethylene-vinyl acetate material) can be cold-formed to form the desired container 86. The pad may typically be easily removable when container 86 is made of polyethylene.

As shown in FIG. 9, the recess wall 88 of container 86 and the patient's skin 74a together enclose soft, elastomeric pad 70a, with the pad of abutting the skin. Container 86 may be secured to the skin by adhesive tape 94.

Pads 70 and 70a may be made, for example, from Versaflex®CL 2003X Thermoplastic Rubber Compound, which is a proprietary, oil-plasticized styrene block copolymer elastomer, manufactured by GLS Corp. of McHenry, Ill. This is a transparent material having a Shore 00 hardness of about 29, an elongation at break of about 1290% (ASTM D412—Die C, 2 hours at 23° C.); a tear strength of about 7 million dynes per cm. (ASTM D624); a tensile strength (English) of 280 psi (ASTM D412—Die C—2 hours at 23° C.); a 100% modulus (English) of about 9 psi (ASTM D 412—Die C, 2 hours at 23° C.) and a 300% modulus of about 15 psi (English) ASTM D 412—Die C, 2 hours at 23° C.). Medicaments, such as clotting agents, disinfectants, or any medically beneficial material may be added to the formulation, if desired.

The pads of this invention may desirably be as clear and transparent as glass so that the wound underneath may be easily monitored without removal of the pad.

Thus, a stick-on injection site or hemostasis device is provided, in which the pad through which injection may be made, if desired, does not have to be retained under compression in a housing to obtain good resealing, although it may be so retained if desired. Accordingly, the pad-type injection site or hemostasis device does not require a rigid housing to hold it in a compressed state, but the pad simply provides spontaneous resealing under most physiological blood pressure conditions, thus greatly reducing loss of blood. Such a pad type injection site is also usable to provide an injection site through a wall of a medical device, while providing good resealing after the needle is withdrawn. Also, typically larger pads of this invention may be used for hemostasis of larger wounds.

The above has been offered for illustrative purposes only, and is not intended to limit the scope of the invention of this application, which is as defined in the claims below.

That which is claimed is:

1. A method of suppressing bleeding at a needle insertion site, comprising the steps of:
    inserting a hollow cannula through a point in skin in a vessel of a patient;
    thereafter placing a soft, elastomeric pad on the skin of the patient to cover the point of the skin through which the cannula penetrates into the vessel; and
    thereafter removing the cannula while simultaneously compressing the pad toward said point in the skin by a force insufficient to collapse the cannulated vessel, said pad having a hardness of no more than about durometer 50 Shore 00, whereby bleeding is immediately terminated and clotting is promoted by the pad.

2. The method of claim 1 is which the soft, elastomeric pad is affixed to the skin of the patient, and the pad is substantially transparent.

3. The method of claim 1 in which the pad is of a solid, domed shape.

4. The method of claim 3 in which said pad of solid, domed shape resides in a dome-shaped recess defined by a dome wall of a plastic sheet, said sheet also having a flat flange at least partially surrounding said dome wall, said flat flange being affixed to the skin of the patient, with the dome wall and the patient's skin together enclosing the soft, elastomeric pad, and the pad abutting the skin.

5. The method of claim 4 in which said flat flange is affixed to the skin through an adhesive layer carried on the flange.

6. The method of claim 4 in which said plastic sheet is made of poly(ethylene-vinyl acetate).

7. The method of claim 4 in which said dome-shaped recess is cold formed in said plastic sheet.

8. The method of claim 4 in which the hardness of said elastomer is no more than about Durometer 30 Shore 00.

9. The method of claim 8 in which said elastomer has a tear resistance of at least about 800,000 dynes per cm.

10. The method of claim 9 in which an elongation to break of said elastomer is at least about 500 percent.

11. The method of claim 1 in which said pad has a glass-smooth face in contact with the skin.

12. The method of claim 1 in which said pad resides in a recess, defined by a recess wall of a plastic sheet, said sheet also having a flat flange at least partially surrounding said recess wall, said flat flange being affixed to the skin of the patient, with the recess wall and the patient's skin together enclosing the soft, elastomeric pad, and the pad abutting the skin.

13. The method of claim 12 in which said flat flange is affixed to the skin through an adhesive layer carried on the flange.

14. The method of claim 12 in which said plastic sheet is made of poly(ethylene-vinyl acetate).

15. The method of claim 1 in which the soft, elastomeric pad is affixed against the skin by an adhesive member extending over the pad on the skin to press the pad against the skin.

16. The method of claim 15 in which the pad is substantially transparent.

17. A flexible, hemostasis pad having a flat non-porous surface immediately terminating bleeding upon application of said flat, non-porous surface to a bleeding vessel at a pressure insufficient to collapse said bleeding vessel, said pad having a rounded, convex outer surface, and a hardness of no more than about durometer 50 Shore 00, wherein a central portion of said pad is at least twice as thick as a peripheral portion of the pad at the edge of the pad.

18. A flexible, hemostasis pad having a non-porous surface immediately terminating bleeding upon application of said pad to a bleeding vessel at a pressure insufficient to collapse said bleeding vessel, said pad having a rounded, convex outer surface, and a hardness of no more than about durometer 50 Shore 00, the pad being substantially transparent, wherein a central portion of said pad is at least twice as thick as a peripheral portion of the pad at the edge of the pad.

19. The pad of claim 18 in which said non-porous surface is a flat surface.

20. A flexible, hemostasis pad having a non-porous surface immediately terminating bleeding upon application of said pad to a bleeding vessel at a pressure insufficient to collapse said bleeding vessel, said pad having a rounded, convex outer surface, and a hardness of no more than about durometer 50 Shore 00, wherein the pad comprises an elastomeric material, and said pad is substantially transparent and has a central portion which is substantially at least twice as thick as a peripheral portion of the pad at the edge of the pad.

21. The pad of claim 20 in which the non-porous surface is a flat surface.

22. A method of suppressing bleeding at a needle insertion site, comprising the steps of:
    inserting a hollow cannula through a point in the skin of a patient to cannulate a vessel;
    positioning a nonporous surface of a substantially transparent, soft pad against the skin of the patient to cover the point on the skin through which the cannula penetrates, and thereafter removing the cannula, while simultaneously during the removal process pressing said pad against said point and surrounding skin with a force insufficient to collapse the cannulated vessel, said pad being substantially transparent and having a hardness of no more than about durometer 50 Shore 00, whereby bleeding from said point is immediately terminated and clotting is promoted by the pad.

23. The method of claim 22 in which said pad has a rounded, convex outer surface.

24. The method of claim 22 in which a central portion of the pad is at least twice as thick as a peripheral portion of the pad at the edge.

25. The method of claim 24 in which the pad pressing against the skin at and surrounding the patient is accomplished by an adhesive bearing strap attached to the patient.

26. The method of claim 24 in which said pad pressing against the skin at and surrounding said point is accomplished manually.

27. The pad of claim 22 in which the non-porous surface is a flat surface.

* * * * *